(12) United States Patent
Gimona et al.

(10) Patent No.: US 8,207,115 B2
(45) Date of Patent: Jun. 26, 2012

(54) TREATMENT OF CARTILAGE DISORDERS WITH FGF-18

(75) Inventors: Alberto Gimona, Geneva (CH); Christoph H. Ladel, Nyon (CH); Elmar Vom Baur, Geneva (CH)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 12/374,488

(22) PCT Filed: Aug. 24, 2007

(86) PCT No.: PCT/EP2007/058830
§ 371 (c)(1),
(2), (4) Date: Jan. 21, 2009

(87) PCT Pub. No.: WO2008/023063
PCT Pub. Date: Feb. 28, 2008

(65) Prior Publication Data
US 2010/0016223 A1  Jan. 21, 2010

Related U.S. Application Data

(60) Provisional application No. 60/840,600, filed on Aug. 28, 2006.

(30) Foreign Application Priority Data

Aug. 25, 2006 (EP) .................................... 06119557

(51) Int. Cl.
*A61K 38/18* (2006.01)

(52) U.S. Cl. ........................................................ 514/9.1

(58) Field of Classification Search .................. None
See application file for complete search history.

(56) References Cited

U.S. PATENT DOCUMENTS

| | | | |
|---|---|---|---|
| 5,614,496 | A | 3/1997 | Dunstan et al. |
| 7,432,049 | B2 | 10/2008 | Liew et al. |
| 2004/0037841 | A1 | 2/2004 | Liew et al. |
| 2005/0043234 | A1 | 2/2005 | Deisher et al. |
| 2006/0172384 | A1 * | 8/2006 | Reardon et al. ............. 435/69.1 |

FOREIGN PATENT DOCUMENTS

WO  WO 2004/032849  4/2004
WO  WO 2006/014444  2/2006

OTHER PUBLICATIONS

Gerwin, N. et al. "Intraarticular drug delivery in osteoarthritis" *Advanced Drug Delivery Reviews*, 2006, pp. 226-242, vol. 58.
Moore, E.E. et al. "Fibroblast growth factor-18 stimulates chondrogenesis and cartilage repair in a rat model of injury—induced osteoarthritis" *OsteoArthritis and Cartilage*, 2005, pp. 623-631, vol. 13.
Hochberg, M. C. et al. "Guidelines for the Medical Management of Osteoarthritis" *Arthritis & Rheumatism*, Nov. 1995, pp. 1535-1540, vol. 38, No. 11.
Venkataraman, G et al. "Molecular characteristics of fibroblast growth factor receptor—fibroblast growth factor receptor—heparin-like glycosaminoglycan complex" *Proc. Natl. Acad. Sci. USA*, Mar. 1999, pp. 3658-3663, vol. 96.
Pritzker, K. P. H. et al. "Osteoarthritis cartilage histopathology: grading and staging" *OsteoArthritis and Cartilage*, 2006, pp. 13-29, vol. 14, No. 1.

* cited by examiner

*Primary Examiner* — Marianne P Allen
(74) *Attorney, Agent, or Firm* — Saliwanchik, Lloyd & Eisenschenk

(57) ABSTRACT

This invention concerns the treatment of cartilage disorder and osteoarthritis in particular. More specifically, it relates to the use of FGF-18 in treatment regimens of patients having a cartilage disorder such as osteoarthritis, such as for example knee osteoarthritis or secondary hip osteoarthritis. Specifically provided is a preferred treatment scheme comprising once weekly administration of an FGF-18 compound per treatment cycle.

34 Claims, 1 Drawing Sheet

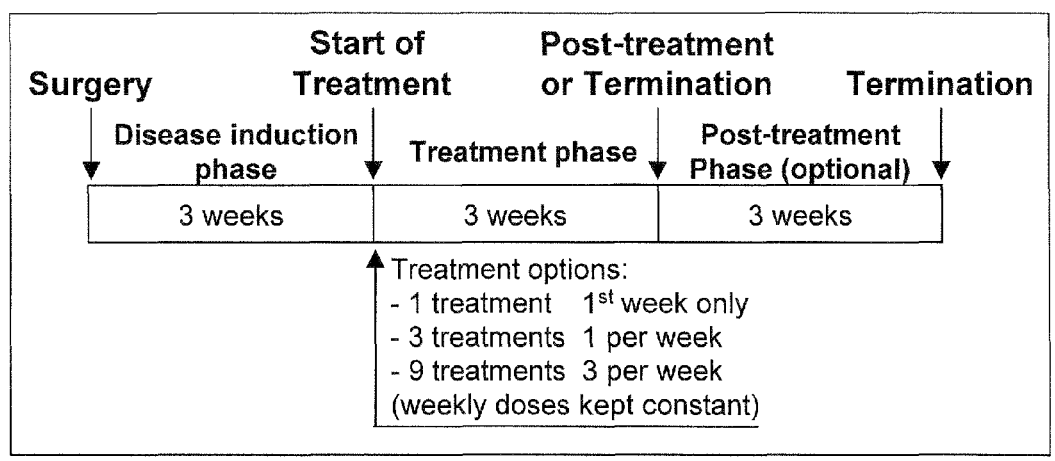

SEQUENCE LISTING

<160> NUMBER OF SEQ ID NOS: 5

<210> SEQ ID NO 1
<211> LENGTH: 624
<212> TYPE: DNA
<213> ORGANISM: Homo sapiens

<400> SEQUENCE: 1

```
atgtattcag cgccctccgc ctgcacttgc ctgtgtttac acttcctgct gctgtgcttc      60
caggtacagg tgctggttgc cgaggagaac gtggacttcc gcatccacgt ggagaaccag     120
acgcgggctc gggacgatgt gagccgtaag cagctgcggc tgtaccagct ctacagccgg     180
accagtggga aacacatcca ggtcctgggc cgcaggatca gtgcccgcgg cgaggatggg     240
gacaagtatg cccagctcct agtggagaca gacaccttcg gtagtcaagt ccggatcaag     300
ggcaaggaga cggaattcta cctgtgcatg aaccgcaaag gcaagctcgt ggggaagccc     360
gatggcacca gcaaggagtg tgtgttcatc gagaaggttc tggagaacaa ctacacggcc     420
ctgatgtcgg ctaagtactc cggctggtac gtgggcttca ccaagaaggg gcggccgcgg     480
aagggcccca agacccggga gaaccagcag gacgtgcatt tcatgaagcg ctaccccaag     540
gggcagccgg agcttcagaa gcccttcaag tacacgacgg tgaccaagag gtcccgtcgg     600
atccggccca cacaccctgc ctag                                            624
```

<210> SEQ ID NO 2

-continued

<211> LENGTH: 207
<212> TYPE: PRT
<213> ORGANISM: Homo sapiens

<400> SEQUENCE: 2

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 3
<211> LENGTH: 624
<212> TYPE: DNA
<213> ORGANISM: Mus musculus

<400> SEQUENCE: 3
atgtattcag cgccctccgc ctgcacttgc ctgtgtttac actttctact gctgtgcttc      60
caggttcagg tgttggcagc cgaggagaat gtggacttcc gcatccacgt ggagaaccag     120
acgcgggctc gagatgatgt gagtcggaag cagctgcgct tgtaccagct ctatagcagg     180
accagtggga agcacattca agtcctgggc cgtaggatca gtgcccgtgg cgaggacggg     240
gacaagtatg cccagctcct agtggagaca gataccttcg ggagtcaagt ccggatcaag     300
ggcaaggaga cagaattcta cctgtgtatg aaccgaaaag gcaagctcgt ggggaagcct     360
gatggtacta gcaaggagtg cgtgttcatt gagaaggttc tggaaaacaa ctacacggcc     420
ctgatgtctg ccaagtactc tggttggtat gtgggcttca ccaagaaggg gcggcctcgc     480
aagggtccca gacccgcga gaaccagcaa gatgtacact tcatgaagcg ttaccccaag     540
ggacaggccg agctgcagaa gcccttcaaa tacaccacag tcaccaagcg atcccggcgg     600
atccgcccca ctcaccccgg ctag                                            624

<210> SEQ ID NO 4
<211> LENGTH: 207
<212> TYPE: PRT
<213> ORGANISM: Mus musculus

```
<400> SEQUENCE: 4

Met Tyr Ser Ala Pro Ser Ala Cys Thr Cys Leu Cys Leu His Phe Leu
1               5                   10                  15

Leu Leu Cys Phe Gln Val Gln Val Leu Ala Ala Glu Glu Asn Val Asp
            20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
        50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Ala Glu Leu Gln Lys Pro Phe Lys Tyr Thr
            180                 185                 190

Thr Val Thr Lys Arg Ser Arg Arg Ile Arg Pro Thr His Pro Gly
        195                 200                 205

<210> SEQ ID NO 5
<211> LENGTH: 170
<212> TYPE: PRT
<213> ORGANISM: Artificial
<220> FEATURE:
<223> OTHER INFORMATION: FGF18(170AA)

<400> SEQUENCE: 5

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
            20                  25                  30

Ser Arg Thr Ser Gly Lys His Ile Gln Val Leu Gly Arg Arg Ile Ser
        35                  40                  45

Ala Arg Gly Glu Asp Gly Asp Lys Tyr Ala Gln Leu Leu Val Glu Thr
    50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
        115                 120                 125

Lys Lys Gly Arg Pro Arg Lys Gly Pro Lys Thr Arg Glu Asn Gln Gln
    130                 135                 140

Asp Val His Phe Met Lys Arg Tyr Pro Lys Gly Gln Pro Glu Leu Gln
```

```
            145                 150                 155                 160
Lys Pro Phe Lys Tyr Thr Thr Val Thr Lys
                    165                 170
```

TREATMENT OF CARTILAGE DISORDERS WITH FGF-18

CROSS-REFERENCE TO RELATED APPLICATION

This application is the U.S. national stage application of International Patent Application No. PCT/EP2007/058830, filed Aug. 24, 2007, which claims the benefit of U.S. Provisional Patent Application No. 60/840,600, filed Aug. 28, 2006, the disclosures of which are hereby incorporated by reference in their entirety, including all figures, tables and amino acid or nucleic acid sequences.

FIELD OF THE INVENTION

This invention is in the field of medicine and concerns the treatment of cartilage disorders and osteoarthritis in particular. More specifically, it relates to the use of FGF-18 in treatment regimens and for the manufacture of a medicament for the treatment of patients having a cartilage disorder such as osteoarthritis, such as for example knee osteoarthritis or secondary hip osteoarthritis. Specifically provided is a preferred treatment scheme comprising once weekly administration of an FGF-18 compound per treatment cycle.

BACKGROUND OF THE INVENTION

FGF18 was identified as a member of the FGF family which was most closely related to FGF8 and FGF17. Activities associated with FGF18 include stimulation of mesenchymal lineage cells, in particular cardiac myocytes, osteoblasts and chondrocytes (U.S. Pat. No. 6,352,971). FGF18 binds and activates FGFR4 and the IIIc splice variant of FGFR3 and FGFR2.

Bone remodeling is the dynamic process by which tissue mass and skeletal architecture are maintained. The process is a balance between bone resorption and bone formation, with two cell types thought to be the major players. These cells are the osteoblasts and osteoclasts. Osteoblasts synthesize and deposit matrix to become new bone. The activities of osteoblasts and osteoclasts are regulated by many factors, systemic and local, including growth factors.

Cartilage is a type of dense connective tissue. It is composed of cells called chondrocytes, which are dispersed in a firm, gel-like ground substance, called the matrix. Cartilage is avascular (contains no blood vessels) and nutrients are diffused through the matrix. Cartilage is found in the joints, the rib cage, the ear, the nose, in the throat and between intervertebral disks. There are three main types of cartilage: hyaline, elastic and fibrocartilage. The main purpose of cartilage is to provide a framework upon which bone deposition could begin. Another important purpose of cartilage is to provide smooth surfaces and mechanical protection for the movement of articulating bones.

Replacement of damaged cartilage, in particular articular cartilage, caused either by injury or disease is a major challenge for physicians, and available treatments are considered unpredictable and effective for only a limited time. Virtually all currently available treatments for cartilage damage focus on pain relief, with little or no efficacy on regeneration of damaged tissues. Therefore, the majority of younger patients either do not seek treatment or are counseled to postpone treatment for as long as possible. When treatment is required, the standard procedure is total joint replacement or microfracture, a procedure that involves penetration of the subchondral bone to stimulate fibrocartilage deposition by chondrocytes.

For patients with osteoarthritis, non-surgical treatment consists of physical therapy, lifestyle modification (e.g. reducing activity), bracing, supportive devices, oral and injection drugs (e.g. non-steroidal anti-inflammatory drugs), and medical management. Surgical options are very specific to osteoarthritis severity and can provide a reduction in symptoms that are generally only short lived. Tibial or femoral osteotomics (cutting the bone to rebalance joint wear) may reduce symptoms, help to maintain an active lifestyle, and delay the need for total joint replacement. Total joint replacement can provide relief for the symptom of advanced osteoarthritis, but generally requires a change in a patient's lifestyle and/or activity level.

Therefore, it would be desirable to have a method for treating, preventing or ameliorating the symptoms of cartilage disorders that would permit regeneration of damaged tissue. In addition, it would be desirable that such method be as safe and effective as possible. Moreover, as cartilage disorders may be chronic diseases, it would be desirable that such method permits re-treatments of the patient.

SUMMARY OF THE INVENTION

The present invention provides a method for treating a patient having a cartilage disorder comprising the administration of an FGF-18 compound wherein the FGF-18 compound is administered at least two times, said administrations being separated by about 4, preferably 5, 6, 7, 8, 9 or 10 days. In preferred embodiments of the invention, the cartilage disorder to be treated is osteoarthritis, the FGF-18 compound is the FGF-18 fragment designated herein as FGF-18(170AA) and the posology cycle is 10 to 30 mcg per intra-articular injection once weekly for 3 consecutive weeks (one treatment cycle). In a preferred embodiment such treatment cycles may be repeated after 4 or 6 months. For example, where a treatment cycle is repeated after 6 months, if a first treatment cycle is started e.g. in January of a given year, then a second treatment cycle may be started in July of said year.

Further provided herein is the use of an FGF-18 compound in the manufacture of a medicament for the treatment of a patient having a cartilage disorder wherein the FGF-18 compound is administered at least two times, said administrations being separated by about 4, preferably 5, 6, 7, 8, 9 or 10 days. Also provided herein is the use of an FGF-18 compound for the treatment of a patient having a cartilage disorder wherein the FGF-18 compound is administered at least two times, said administrations being separated by about 4, preferably 5, 6, 7, 8, 9 or 10 days.

Provided herein is also the use of an FGF-18 compound in the manufacture of a medicament for the treatment of a patient having a cartilage disorder, the medicament being adapted to be administered at least two times, said administrations being separated by about 4, preferably 5, 6, 7, 8, 9 or 10 days.

BRIEF DESCRIPTION OF THE FIGURE

FIG. 1 is a treatment regimen for evaluating the effects of FGF-18 on cartilage and injuries.

DETAILED DESCRIPTION OF THE INVENTION

The present invention provides suitable treatment modalities, including suitable administration schemes for the treatment of various cartilage disorders, such as in particular osteoarthritis, with FGF-18 compounds, such as for example the FGF-18(170AA) protein fragment. In the context of the present invention it has been surprisingly found that FGF-18 compounds have optimal disease- or symptom-ameliorating effects on cartilage disorders when administered according to the methods and uses disclosed herein. It has been found that less frequent dosing schedules than contemplated by the present invention may not be fully effective, whereas more frequent dosing than contemplated by the present invention may cause inflammation and/or other counterproductive effects on the cartilage or joint environment when the same or comparable dosages as those contemplated by the present invention are being used.

Accordingly, in one aspect of the present invention there is provided a method for treating a patient having a cartilage disorder comprising the administration of an FGF-18 compound wherein the FGF-18 compound is administered at least two times, said administrations being separated by about 4, preferably 5, 6, 7, 8, 9 or 10 days. For example, where administrations are separated by about 4 days, a second administration may be made about 96 hours after a first administration; e.g. where and administration is given on day 1 in, for example, the morning, there will be 3 calendar days where the patient will not receive an administration (day 2, day 3, day 4) and the patient will again receive an administration on day 5 in the morning.

In a particularly preferred embodiment said administrations are separated by about, 6, 7 or 8 days. In one preferred embodiment they are separated by about 7 days.

In another aspect of the present invention there is provided the use of an FGF-18 compound in the manufacture of a medicament for the treatment of a patient having a cartilage disorder wherein the FGF-18 compound is administered at least two times, said administrations being separated by about 4, preferably 5, 6, 7, 8, 9 or 10 days. In a particularly preferred embodiment said administrations are separated by about, 6, 7 or 8 days. In one preferred embodiment they are separated by about 7 days.

In a preferred embodiment said administrations are separated by about 7 days each. Preferably, the FGF-18 compound is administered in regular intervals once per week.

In an embodiment of the present invention there is provided the use of an FGF-18 compound in the manufacture of a medicament for the treatment of a patient having a cartilage disorder the medicament being adapted to be administered at least two times, said administrations being separated by about 4, preferably 5, 6, 7, 8, 9 or 10 days. In a particularly preferred embodiment said administrations are separated by about, 6, 7 or 8 days. In one preferred embodiment they are separated by about 7 days.

In a preferred embodiment said administrations are separated by about 7 days each. Preferably, the FGF-18 compound is administered in regular intervals once per week.

In a preferred embodiment the FGF-18 compound is administered for at least 2 consecutive weeks, at least 3 consecutive weeks or at least 4 consecutive weeks per treatment cycle. In a preferred embodiment a treatment cycle is a number of consecutive weeks wherein an FGF-18 compound is given each week. In a further preferred embodiment the FGF-18 compound is administered for 2 consecutive weeks, 3 consecutive weeks or 4 consecutive weeks per treatment cycle, and such treatment may comprise 1, 2, 3, 4, 5 or 6 treatment cycles per year. In one preferred embodiment the FGF-18 compound is administered for 3 consecutive weeks per treatment cycle. In one preferred embodiment such treatment comprises 2 treatment cycles per year.

In a preferred embodiment the treatment comprises intra-articular administration of the FGF-18 compound. Alternatively, the treatment may comprise intravenous administration of the FGF-18 compound.

In a further preferred embodiment the treatment comprises administration at a dose of 1-100 mcg, or preferably 1-60 microgram (mcg), or preferably 3-50 mcg, or preferably 5-40 mcg, or preferably 10-30 mcg per single intra-articular administration of the FGF-18 compound. In a preferred embodiment the treatment comprises administration at a dose of about 3, 5, 10, 15, 20, 25, 30, 35, 40, 45, 50, 55, 60 mcg per single intra-articular administration of the FGF-18 compound. Preferred doses include 5, 10, 15, 20, 25 and 30 per single intra-articular administration of the FGF-18 compound.

In a further preferred embodiment the treatment comprises administration at a dose of 50-200 mcg/kg, preferably 80-120 mcg/kg per single intravenous administration of the FGF-18 compound. In a preferred embodiment the treatment comprises administration at a dose of 80, 90, 100, 110 or 120 mcg/kg per single intravenous administration of the FGF-18 compound.

In a preferred embodiment the cartilage disorder treated by any of the methods of the invention is osteoarthritis, such as for example osteoarthritis which is classified as stage II or stage III according to OARSI. In a preferred example the osteoarthritis may be knee osteoarthritis or hip osteoarthritis, such as secondary hip osteoarthritis. The skilled person is fully aware of osteoarthritis classifications that are used in the art. In particular, the OARSI classification is known in the art. The skilled person may reference the "Guidelines for the medical management of osteoarthritis" (Marc C. Hochberg, Roy D. Altman, Kenneth D. Brandt, Bruce M. Clark, Paul A. Dieppe, Marie R. Griffin, Roland W. Moskowitz, Thomas J. Schnitzer, Arthritis & Rheumatism, Volume 38, Issue 11, 1995. Pages 1535-1546.)

Preferred FGF-18 compounds of the invention are selected from human wildtype FGF-18 or FGF-18(170AA).

Compounds of the Invention

Native or wildtype FGF-18 is a protein expressed by chondrocytes of articular cartilage. The present invention generally relates to the use of an Fibroblast Growth Factor 18 (FGF-18) in the treatment of osteoarthritis. An FGF-18 compound of the invention includes for example native or wildtype FGF-18, in particular human FGF-18, bioactive variants thereof, such as bioactive allelic variants, and bioactive truncated forms of FGF-18. The present invention may relate to any variant or modified from of FGF-18 which retains the desired FGF-18 bioactivity as herein described, such as in particular the increase in cartilage deposition. Bioactivities of FGF-18 include in particular those described in the Examples hereinbelow, such as in particular in the in vivo disease models described herein.

The nucleotide sequence of the human FGF-18 cDNA is described in SEQ ID NO. 1, and its deduced amino acid sequence is described in SEQ ID NO. 2. FGF18 was originally designated zFGF-5, and is fully described in U.S. Pat. Nos. 6,352,971, 5,989,866 and US Patent Application Publication US2005/0043234, all of which are incorporated herein by reference. Analysis of the cDNA encoding a human FGF18 polypeptide (SEQ ID NO: 1) revealed an open reading frame encoding 207 amino acids (SEQ ID NO: 2) comprising a mature polypeptide of 180 amino acids (residue 28 to residue 207 of SEQ ID NO: 2).

The mouse FGF-18 polynucleotide sequence as shown in SEQ ID NO: 3 and corresponding amino acid sequence as shown in SEQ ID NO: 4 were found to have a high degree of homology to that of the human ortholog. At the amino acid level, the mouse and human polypeptides are approximately 98% identical, with three amino acid changes. Those skilled in the art will recognize that the sequences disclosed in SEQ ID NO: 1 or SEQ ID NO: 3 and SEQ ID NO: 2 and SEQ ID NO: 4 represent a single allele of the human and mouse FGF18 gene and polypeptide, respectively, and that allelic variation and alternative splicing are expected to occur.

As already mentioned, FGF-18 compound of the invention includes for example native or wildtype FGF-18, in particular human FGF-18, bioactive variants thereof, such as bioactive allelic variants, and bioactive truncated forms of FGF-18. The present invention may relate to any variant or modified from of FGF-18 which retains the desired FGF-18 bioactivity as herein described, such as in particular the increase in cartilage deposition.

In an embodiment of the present invention FGF-18 compound is a truncated form of human FGF-18. In a particular embodiment said truncated form of FGF-18 comprises or consists of residues 28 to 175 of SEQ ID NO: 2, or a functional derivative, or variant or mutein as defined herein. In another embodiment said truncated form of FGF-18 comprises or consists of residues 28 to 176, 28 to 177, 28 to 178, 28 to 179, 28 to 180, 28 to 181, 28 to 182, 28 to 183, 28 to 184, 28 to 185, 28 to 186, 28 to 187, 28 to 188, 28 to 189, 28 to 190, 28 to 191, 28 to 192, 28 to 193, 28 to 194 or 28 to 195, 28 to 196, 28 to 197, 28 to 198, 28 to 199, 28 to 200, 28 to 201, 28 to 202, 28 to 203, 28 to 204, 28 to 205, 28 to 206 or 28 to 207 of SEQ ID NO: 2, or a functional derivative, or a variant or mutein as defined herein. These polypeptides, functional derivative, or variant or mutein may comprise an additional N-terminal amino acid residue, preferably a methionine. Indeed, depending on the expression system and conditions, polypeptides of the invention may be expressed in a recombinant host cell with a starting Methionine.

A preferred embodiment of the present invention is a truncated form of FGF-18, containing 170 amino acids (AA), hereinafter also designated as "FGF-18(170AA)". The wild type or naturally occurring form is 207 AA long of which the first 27 AA are the signal sequence and the last 11 AA are deleted in FGF-18(170AA) (as can be demonstrated also for natural occurring FGF-18 in vivo). FGF-18(170AA) may be expressed in E. coli, as there is no signal sequence and the AA sequence starts with a methionine followed by AA28 and ends with AA196. The molecular weight of FGF-18(170AA) is 19.83 kDa, pI~10. FGF-18(170AA) is further described in SEQ ID NO: 5 hereinbelow. FGF-18(170AA) increases chondrocyte proliferation/differentiation and cartilage deposition leading to repair and reconstruction for a variety of cartilaginous tissues.

Members of the FGF family are characterized by heparin binding domains. A putative heparin-binding domain for FGF-18 has been identified in the region of amino acid residue 148 (Gly) to amino acid residue 169 (Gln) of SEQ ID NO: 2 and SEQ ID NO: 4. It is postulated that receptor-mediated signaling is initiated upon binding of FGF ligand complexed with cell-surface heparin sulfate proteoglycans.

Many FGF family members can be placed into one of two related families on the basis of their structures and functions. aFGF and bFGF consist of three exons separated by two introns of variable length. FGF-18 consists of five exons, the first three of which correspond to the first exon of aFGF and bFGF. All known FGF family members are spliced to form single polypeptides.

Analysis of the ligand-receptor complex of FGF-18 has demonstrated that FGF18 has specificity for FGFR4 and the "IIIc" splice variants of FGFR3 and FGFR2. FGFR3-IIIc and FGFR2-IIIc are expressed by chondrocytes of cartilage tissue, and in particular, both receptors have been found within human articular cartilage. FGFR3 and FGFR2 have been found in the growth plate of mammals and play important roles in the formation of endochondral and intramembranous bone. FGFR2 is first expressed in condensing mesenchyme and FGFR3 expression is initiated as chondrocytes differentiate and proliferate. In developing cranial bones, FGFR3 is found in the dura mater and periosteum, whereas FGFR2 is expressed in osteoprogenitor cells at the osteogenic front separating the sutures. FGFR2 is also expressed in traebecular bone. Previously, it has been shown that FGF18 is a proliferative agent for chondrocytes and osteoblasts, depending upon both the differentiated state of these cell types and the mode of administration. (See, U.S. Pat. Nos. 6,352,971 and 5,989,866; Ellsworth et al. Osteoarthritis and Cartilage, 10: 308-320, 2002; Shimoaka et al., J. Bio. Chem. 277 (9) 7493-500, 2002).

Preferably, the FGF-18 compound of the invention increases cartilage deposition. Such increase may be measured both in vivo and in vitro. Generation of hyaline cartilage, elastic cartilage, and fibrocartilage are valuable both as a therapeutic and as component for biological matrices. FGF-18 compounds, such as FGF-18(170AA), and compositions containing FGF-18 compounds ("FGF-18 compositions") will be useful in treating articular cartilage defects in synovial joints that are due to age-related superficial fibrillation, cartilage degeneration due to osteoarthritis, and focal chondral and osteochondral defects due to injury or disease.

FGF-18 compounds and compositions may also be useful for treating joint disease caused by osteochondritis dissecans and degenerative joint disease. In the field of reconstructive and plastic surgery, FGF-18 compositions will be useful for autogenous or allogenic cartilage expansion and transfer for reconstruction of extensive tissue defects.

FGF-18 compounds and compositions may also be useful to expand cells and induce elastic cartilage production. Expansions of cells and induction of elastic cartilage production will be useful for generation and repair of ear and nose tissue. FGF-18 compounds and compositions can also be used to expand chondrocyte populations in culture for autogenous or allogenic chondrocyte transplantation and then administered with or without concurrent treatment consisting of administration of FGF-18 compositions. In these procedures, for example, chondrocytes can be harvested arthroscopically from an uninjured minor load-bearing area of the damaged joint, and can be cultured in the presence of FGF18 compositions to increase the number of cells prior to transplantation. The expanded cultures will then be admixed with FGF-18 compositions, and placed in the joint space or directly into the defect. FGF-18 compositions can be used in combination with periosteal or perichondrial grafts that contain cells that can form cartilage and/or help to hold the transplanted chondrocytes or their precursor cells in place. FGF-18 compositions can be used to repair cartilage damage in conjunction with lavage of the joint, stimulation of bone marrow, abrasion arthroplasty, subchondral drilling, or microfracture of the subchondral bone. Additionally, after the growth of cartilage due to the administration of the FGF-18 composition, additional surgical treatment may be necessary to suitably contour the newly formed cartilage surface.

An FGF-18 compound according to the present invention may also be a functional derivative, variant or mutein of a wildtype FGF-18 protein.

"Functional derivatives" as used herein cover derivatives of FGF-18, and its variants or muteins and fused proteins, which may be prepared from the functional groups which occur as side chains on the residues or the N or C terminal groups, by means known in the art. These functional derivatives are included in the invention as long as they remain pharmaceutically acceptable, i.e. they do not destroy the activity of the protein, which is substantially similar to, or better than, the activity of FGF-18, and do not confer toxic properties on compositions containing it.

These derivatives may, for example, include polyethylene glycol side chains, which may improve other properties of the protein, such as stability, half-life, bioavailability, tolerance by the human body, or reduce immunogenicity. To achieve this goal, FGF-18 may be linked e.g. to Polyethlyenglycol (PEG). PEGylation may be carried out by known methods, as for example described in WO 92/13095. In particular, PEG-IFN can be prepared in accordance with the teaching of WO 99/55377.

Therefore, in a preferred embodiment, the functional derivative of FGF-18 comprises at least one moiety attached to one or more functional groups, which occur as one or more side chains on the amino acid residues. An embodiment in which the moiety is a polyethylene glycol (PEG) moiety is highly preferred. In accordance with the present invention, several PEG moieties may also be attached to the FGF-18.

Other derivatives include a modified FGF-18 protein, such as a long-acting form of FGF-18. In particular, the long-acting FGF-18 may be selected from pegylated FGF-18, FGF-18-HAS fusion proteins, and FGF-18-Fc-fusion proteins.

Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

"Variants" or "muteins", as used in the frame of the present invention, refer to analogs of FGF-18, in which one or more of the amino acid residues of natural FGF-18 are replaced by different amino acid residues, or are deleted, or one or more amino acid residues are added to the natural sequence of FGF-18, without diminishing considerably the activity of the resulting products as compared with the wild type FGF-18. These muteins are prepared by known synthesis and/or by site-directed mutagenesis techniques, or any other known technique suitable therefor.

The "variant" or "mutein" in accordance with the present invention include proteins encoded by a nucleic acid, such as DNA or RNA, which hybridizes to DNA or RNA encoding FGF-18 as disclosed e.g. in U.S. Pat. No. 5,989,866 under stringent conditions. The term "stringent conditions" refers to hybridization and subsequent washing conditions, which those of ordinary skill in the art conventionally refer to as "stringent". See Ausubel et al., Current Protocols in Molecular Biology, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30 60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology and/or similarity of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

The "variant" or "mutein" in accordance with the present invention include proteins having a sequence of amino acids sufficiently duplicative of that of FGF-18, such as to have substantially similar activity to FGF-18.

In a preferred embodiment, any such variant or mutein has at least 40% identity or homology with the sequence of FGF-18. More preferably, it has at least 50%, at least 60%, at least 70%, at least 80% or, most preferably, at least 90% identity or homology thereto.

Muteins of FGF-18, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of FGF-18 polypeptides may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of FGF-18 for use in the present invention include any known method steps, such as presented in U.S. Pat. Nos. 4,959,314, 4,588,585 and 4,737,462 to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

Formulation of an FGF18-Compound and Administration

FGF-18 compounds may be formulated as a pharmaceutical composition, i.e. together with a pharmaceutically acceptable carrier, excipients or the like. The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution. Such formulations of FGF-18 compounds including at least one further pharmaceutically acceptable carrier, excipients or the like are herein also referred to as "FGF-18 compositions".

FGF-18 compounds and compositions can be applied by direct injection into the synovial fluid of the joint or directly into the defect, either alone or complexed with a suitable carrier for extended release of protein (such as for example suitable excipients for slow-release formulations, such as e.g. cyclodextrin) or restricted local release (such as, for example, delivery through biocompatible sponges, similar bio-matrixes, encapsulated cells or the like).

Formulations for intraarticular (IA) application will comply with most of the requirements that also apply to other injection formulations, i.e., they need to be sterile and compatible with the physiological conditions at the application site (e.g., knee joint, SF). The sterility of solution formulations can be achieved by autoclaving (if all components of the formulation are sufficiently resistant to thermal stress) or sterile filtration, while for other formulations, the manufacturing processes required for ensuring a sterile product may be more complex. For example, sterile filtration is not feasible for formulations containing particles (suspensions), semisolid or solid formulations. For compatibility of the formulation with the physiological conditions at the site of injection, the characteristics of the SF have to be taken into consideration. Preferably formulations of the invention therefore are isotonic. The pH of the formulations is either close to the pH of SF (i.e., pH 7.4) or slightly lower, but preferably not below pH ~5.5, to allow for optimum stability of the active ingredient, while minimizing possible side effects of non-physiological pH values such as activation of proteolytic enzymes, e.g., cathepsins. The excipients used for IA injection may also be present in other injection formulations, e.g., for intramuscular or subcutaneous application.

In an embodiment of the present invention, the mode of administration of the FGF-18 compound described herein is selected from the group consisting of: intra-auricular administration, peri-auricular administration, intra-nasal administration, peri-nasal administration, endosinusial administration, intra-costal administration, peri-costal administration, intra-thoracic administration, peri-thoracic administration, epidural administration, peri-vertebral administration, peri-synovial administration, intra-synovial administration, endosinusial administration, peri-articular administration and intra-articular administration. In a preferred embodiment, the FGF-18 compound described herein is administered peri-articularly (administration around a joint) or intrarticularly (administration within a joint). In an embodiment of the present invention, the periarticular or intraarticular administration is done around or in a joint selected from joint of the hip, knee, elbow, wrist, ankle, spine, feet, finger, toe, hand, shoulder, ribs, shoulder blades, thighs, shins, heels and along the bony points of the spine. In yet another preferred embodiment the periarticular or intraarticular administration is done around or in a the joint of the hip or the knee.

Cartilage Disorders

The present invention relates to methods of treating, preventing or ameliorating the symptoms of a cartilage disorder in a mammal. Preferably such cartilage disorder result from damages due to traumatic injury or chondropathy. It is understood that preferably humans are patients to be treated according to the present invention; however, it is understood that other mammals, including but not limited to dogs, horses and the like may be treated with methods according to the present invention.

Examples of cartilage disorders that may be treated, prevented or ameliorated by the treatment described herein include but are not restricted to: arthritis, osteochondritis, costochondritis (such as Tietze'syndrome), osteomyelitis, polychondritis, relapsing polychondritis and Osteochondritis Dissecans.

In an embodiment of the present invention, the cartilage disorder treated, prevented or ameliorated is arthritis. Preferably, said disease is selected from the group consisting of: ankylosing spondylitis, diffuse idiopathic skeletal hyperostosis (DISH), gout, pseudogout, infectious arthritis, osteoarthritis, rheumatoid arthritis, psoriatic arthritis, reactive arthritis, scleroderma, Sjögren's syndrome and Still's disease. In a preferred embodiment, the cartilage disorder treated, prevented or ameliorated is Rheumatoid arthritis or osteoarthritis. In a particularly preferred embodiment, the cartilage disorder treated, prevented or ameliorated is osteoarthritis.

Arthritis, relates to a damage to articular structures (joints) in the body and related inflammatory processes. Arthritis, including osteoarthritis, rheumatoid arthritis, arthritic joints as a result of injury, and the like, are common inflammatory conditions which would benefit from the therapeutic use of FGF18 according to the present invention.

In an embodiment of the present invention, the cartilage disorder treated, prevented or ameliorated is ankylosing spondylitis. Ankylosing spondylitis (AS) is arthritis involving the spine. It causes pain and stiffness in the back, and also a bent posture. This is a result of ongoing swelling and irritation of the spinal joints (vertebrae). In severe cases, inflammation of the vertebrae can eventually cause them to fuse together leading to severely limited mobility. Inflammation of the tendons and ligaments that connect and provide support to joints can lead to pain and tenderness in the ribs, shoulder blades, hips, thighs, shins, heels and along the bony points of the spine.

Ankylosing spondylitis is a chronic inflammatory form of arthritis that affects the spinal joints. The hallmark feature of AS is the involvement of the joints at the base of the spine where the spine joins the pelvis—the sacroiliac (SI) joints.

The disease course is highly variable, and while some individuals have episodes of transient back pain only, others have more chronic severe back pain that leads to differing degrees of spinal stiffness over time. In almost all cases the disease is characterized by acute painful episodes and remissions (periods where the problem settles).

Over the years AS has been known by many different names including poker back, rheumatoid spondylitis, and Marie-Strumpells spondylitis. Since the early 70s with increasing knowledge about the disease, there is almost universal use of the term ankylosing spondylitis. AS is a member of the family of diseases that attack the spine.

In an embodiment of the present invention, the cartilage disorder treated, prevented or ameliorated is diffuse idiopathic skeletal hyperostosis. Diffuse idiopathic skeletal hyperostosis (DISH) is characterized by excessive bone growth along the sides of the vertebrae of the spine. It also involves inflammation and bone growth where tendons and ligaments attach to bone, such as at the elbow, knee and the heel of the foot. Bone spurs are common among people with DISH.

DISH (sometimes called Forestier's disease) is considered a form of degenerative arthritis and is characterized by excessive bone growth along the sides of the vertebrae of the spine. It is also associated with inflammation and calcification (bone growth) at other areas of the body where tendons and ligaments attach to bone, such as at the elbow, knee and the heel of the foot. These can lead to bone spurs. Heel spurs, for example, are common among people with DISH.

In an embodiment of the present invention, the cartilage disorder treated, prevented or ameliorated is gout. Gout is a type of arthritis in which uric acid, a waste product that occurs naturally occurring within the body, rises above normal levels. Rather than being flushed by the kidneys and through the urine, as it normally is, it forms crystals and deposits in the joints. These deposits give rise to inflammation of the joints, causing pain, swelling, redness and tenderness of the area. Most typically the joint affected is that of the big toe, but gout can also affect the ankle, knee, foot, hand, wrist and elbow. Uric acid crystals may also form deposits in other areas such as under the skin or in other soft tissues, and in the kidney or urinary tract.

Gout typically affects the joint at the base of the big toe. In over half of all initial attacks, this is the first joint affected. Almost any other joint can be affected, but the joints of the lower limbs are more commonly than those of the upper limbs.

The majority of initial gout attacks involve only one joint, and, with treatment, subside within three to ten days. Over 50% of people who have had an acute attack of gout will have a recurrence within the year. Over time the attacks may become more frequent, longer lasting and often involve more joints.

For some people the attacks linger, and the disease becomes chronic. The crystals of uric acid deposited inside the joint and in the surrounding soft tissues lead to destructive changes in the joint and cause persistent inflammation.

In an embodiment of the present invention, the cartilage disorder treated, prevented or ameliorated is pseudogout. Pseudogout is a type of arthritis that is caused by the build up of calcium in the body. Pseudogout results from a build up of calcium crystals (calcium pyrophosphate dihydrate) in a joint. The calcium forms crystals that deposit in the joints between bones. This causes swelling and pain in the area. The calcium deposits and chronic inflammation can cause parts of the joint structure to weaken and break down.

With pseudogout cartilage can begin to crack and get holes in it and cause more pain and swelling in the joint. Over time the cartilage may wear away entirely, and the bones rub together.

Much of the pain of pseudogout is a result of muscles and the other tissues that help joints move (such as tendons and ligaments) being forced to work in ways for which they were not designed, as a result of damage to the cartilage. Cartilage itself does not have nerve cells, and therefore cannot sense pain, but the muscles, tendons, ligaments and bones do. After many years of cartilage erosion, bones may actually rub together. This grinding of bone against bone adds further to the pain. Bones can also thicken and form growths, called spurs or osteophytes, which rub together.

Like the disease gout, pseudogout can come on as sudden, recurrent attacks of pain and swelling in a single joint.

In an embodiment of the present invention, the cartilage disorder treated, prevented or ameliorated is infectious arthritis. Infectious arthritis causes pain and swelling in the joints. The inflammation is caused by a germ. The germ can be a bacterium, a virus, or a fungus. There is usually only one joint involved, though sometimes two or three joints can become infected. It does not usually last a long time if it is treated early.

Mostly, infectious arthritis affects the large joints (shoulders, hips, knees), but smaller joints (fingers, ankles) can also be involved.

In a preferred embodiment of the present invention, the cartilage disorder treated, prevented or ameliorated is osteoarthritis. Osteoarthritis is the most common form of arthritis. It may be caused by the breakdown of cartilage. Bits of cartilage may break off and cause pain and swelling in the joint between bones. Over time the cartilage may wear away entirely, and the bones will rub together.

Osteoarthritis can affect any joint but usually concerns hands and weight-bearing joints such as hips, knees, feet, and spine.

The disease state of osteoarthritis (OA) is a complex, multi-factorial progressive disease that is non-inflammatory in nature and which is characterized by a general age-related degradation of articular cartilage in the joints. OA is also characterized by chondrocyte activation leading to cell proliferation and apoptosis, protease expression and abnormal matrix production, failed cartilage repair leading to loss of extracellular matrix, matrix calcification and osteophyte formation. The degradation of cartilage and extracellular matrix structures leads to increased friction between the bones and nerves of the affected joints. OA causes varying levels of pain and progressive debilitation in those afflicted with the disease. Current therapies for OA are palliative or surgical.

In healthy joints cartilage acts as a shock absorber when weight is put on the joint. The slippery surface of the cartilage allows the bones to move smoothly. When a joint develops osteoarthritis the cartilage gradually becomes rough and thin, and the bone underneath thickens.

Although there is usually no swelling in the early stage of the disease, as the arthritis progresses there can be inflammation. Bits of cartilage may break off and float around inside the joint. This disturbs other soft tissues inside the joint and can cause pain and swelling between bones.

Over time as the cartilage wears down, the bones may form bumps on their ends. These bumps are called spurs. Or, the cartilage may wear away entirely, and bones may directly come in contact with each other.

OA may lead to other problems such as: the muscles that hold the joint in place weaken because they are not being used, over time the joint looses its shape and does not work at all.

OA commonly affects weight-bearing joints such as hips, knees, feet and spine. However, non-weight bearing joints such as finger joints and the joint at the base of the thumb may be affected as well. It usually does not affect other joints, except when they have been injured or been put under unusual stress.

In an embodiment of the present invention, the cartilage disorder treated, prevented or ameliorated is rheumatoid arthritis. Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid is infiltrated by similar cells with the addition of numerous neutrophils. Tissues affected are primarily the joints, often in symmetrical pattern. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement. Therefore RA may lead to severe disability and increased mortality.

Joint damage can occur even in cases where the pain is not severe. It can happen even in the early stages of the disease. For many people with RA, damage has shown up on X-rays of the hands and feet within two years of the onset of the disease. But it may be too late to treat by the time X-rays discover the problem.

Severe damage can lead to permanent joint deformity and disability. Pain and swelling may cause difficulty walking.

A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis.

One important way to distinguish RA from other forms of arthritis is by the pattern of joint involvement. For example, RA affects the wrist and many of the hand joints but usually not the joints that are most distal joints.

In RA, the joints tend to be involved in a symmetrical pattern. That is, if the knuckles on the right hand are inflamed, the knuckles on the left hand are likely to be inflamed as well.

Other joints commonly affected by RA include the elbows, shoulders, neck, jaw, feet, ankles, knees, and hips. Other than the neck, the spine usually is not directly affected by RA.

In an embodiment of the present invention, the cartilage disorder treated, prevented or ameliorated is psoriatic arthritis. Psoriatic arthritis is a condition that causes swelling and pain in and around the joints. It also causes a scaly rash on the skin.

It can affect a number of joints including the fingers, wrists, toes, knees, ankles, elbows and shoulder joints, the spine and joints in the lower back (called sacroiliac joints).

Psoriatic arthritis also affects tissues surrounding the joints including tendons and ligaments. It may cause swelling of a whole digit called "sausage" finger or toe. There is also skin inflammation, particularly on the elbows, knees and scalp. Psoriatic arthritis is linked to psoriasis, a disorder causing areas of the skin to become inflamed and be covered with silvery or grey scales.

In an embodiment of the present invention, the cartilage disorder treated, prevented or ameliorated is reactive arthritis. Reactive arthritis refers to pain, stiffness, redness or swelling in a joint resulting from a previous infection. It most often occurs in the joints of the lower limbs (knees, ankles, toes), but can also occur in the upper limbs. Problems may be in the joints only or involve other body systems such as the eyes, skin muscles or tendons. When it affects areas besides the joints, reactive arthritis is then called Reiter's syndrome.

In an embodiment of the present invention, the cartilage disorder treated, prevented or ameliorated is scleroderma. Scleroderma is a condition where the skin gets thick and hard. There are two main types of scleroderma. One type is localized scleroderma, which affects mainly the skin. It can also involve the muscles and joints. The other type, generalized scleroderma, affects the skin as well as the internal organs, such as the heart, lungs and kidneys.

The most characteristic feature of scleroderma is the build-up of tough scar-like fibrous tissue in the skin. Less visible changes include damage to the cells lining the walls of small blood vessels. This may in turn damage major organs.

In an embodiment of the present invention, the cartilage disorder treated, prevented or ameliorated is Sjögren's syndrome. Sjögren's syndrome is a chronic disorder that causes damage to the salivary glands resulting in dry mouth, and the tear glands, resulting in dry eyes. It can also affect other parts of the body including joints, muscles and nerves, organs such as the lungs, kidneys, liver, pancreas, stomach and brain, or glands such as the thyroid gland. Sjögren's syndrome can cause complete destruction of any of these areas. Since Sjögren's syndrome can affect the liver and pancreas, there is a greater chance of developing cancer of the lymph tissue. However, this is an unusual and rare result.

Sjögren's syndrome can occur in two ways. It is 'secondary' Sjögren's syndrome when it occurs in people who have a rheumatic condition or connective tissue disease such as lupus, scleroderma or polymyositis. It is named 'primary' Sjögren's syndrome when dry eyes and mouth are not associated with a rheumatic condition.

In an embodiment of the present invention, the cartilage disorder treated, prevented or ameliorated is Still's disease. Still's disease is a form of arthritis characterized by high spiking fevers, salmon-coloured rashes and inflammation of the joints. The disease is most common among children, for whom it is commonly referred to as systemic juvenile idiopathic arthritis. Still's disease can also occur among adults, although much less commonly than for children. In this case it is referred to as adult-onset Still's disease or AOSD.

As disclosed here above, cartilage disorders that may be treated, prevented or ameliorated by the treatment described herein include: Osteochondritis Dissecans, costochondritis (such as Tietze'syndrome), osteomyelitis, and relapsing polychondritis.

In an embodiment of the present invention, the cartilage disorder treated, prevented or ameliorated is Osteochondritis Dissecans. Osteochondritis dissecans (OCD) is a term for osteochondral fracture. An osteochondral fragment may be present in situ, incompletely detached, or completely detached. OCD is a form of osteochondrosis limited to the articular epiphysis. Articular epiphyses fail as a result of compression. Both trauma and ischemia probably are involved in the pathology. Trauma is most likely the primary insult, with ischemia as secondary injury.

Trauma may be caused by direct trauma, such as impaction fracture, or repetitive microtrauma, such as excessive normal compressive stress.

The knee joint is the most commonly involved site. However, the elbow joint, the ankle joint, tarsal navicular, hip joint, shoulder joint, Glenoid, wrist joint may also be affected.

OCD tends to affect young patients. In OCD of the elbow, patient age averages 23 years and ranges from 4-47 years. In the ankle, patient age averages 20 years and ranges from 8-50 years. In the hip, patient age averages 24 years and ranges from 14-39 years.

Patients usually report pain at the extremes of motion range. Periarticular edema often is present with slight warmth to the touch. When a lower extremity is involved, patients often limp. Symptoms usually improve with protected immobilization of the joint.

In an embodiment of the present invention, the cartilage disorder treated, prevented or ameliorated is costochondritis. Costochondritis is an inflammation of the junctions where the upper ribs join with the cartilage that holds them to the breastbone or sternum. The cause is usually unknown. When the pain of costochondritis is accompanied by swelling it is referred to as Tietze's syndrome.

In an embodiment of the present invention, the cartilage disorder treated, prevented or ameliorated is osteomyelitis. Osteomyelitis is an acute or chronic inflammatory process of the bone and its structures secondary to infection with pyogenic organisms.

The infection associated with osteomyelitis may be localized or it may spread through the periosteum, cortex, marrow, and cancellous tissue. The bacterial pathogen varies on the basis of the patient's age and the mechanism of infection.

Hematogenous osteomyelitis is an infection caused by bacterial seeding from the blood. Acute hematogenous osteomyelitis is characterized by an acute infection of the bone caused by the seeding of the bacteria within the bone from a remote source. This condition occurs primarily in children. The most common site is the rapidly growing and highly vascular metaphysis of growing bones. The apparent slowing or sludging of blood flow as the vessels make sharp angles at the distal metaphysis predisposes the vessels to thrombosis and the bone itself to localized necrosis and bacterial seeding. Acute hematogenous osteomyelitis, despite its name, may have a slow clinical development and insidious onset.

Direct or contiguous inoculation osteomyelitis is caused by direct contact of the tissue and bacteria during trauma or surgery. Direct inoculation (contiguous-focus) osteomyelitis is an infection in the bone secondary to the inoculation of organisms from direct trauma, spread from a contiguous focus of infection, or sepsis after a surgical procedure. Clinical manifestations of direct inoculation osteomyelitis are more localized than those of hematogenous osteomyelitis and tend to involve multiple organisms.

Additional categories include chronic osteomyelitis and osteomyelitis secondary to peripheral vascular disease. Chronic osteomyelitis persists or recurs, regardless of its initial cause and/or mechanism and despite aggressive intervention. Although listed as an etiology, peripheral vascular disease is actually a predisposing factor rather than a true cause of infection.

Disease states known to predispose patients to osteomyelitis include diabetes mellitus, sickle cell disease, acquired immune deficiency syndrome (AIDS), IV drug abuse, alcoholism, chronic steroid use, immunosuppression, and chronic joint disease. In addition the presence of a prosthetic orthopedic device is an independent risk factor as is any recent orthopedic surgery or open fracture.

In an embodiment of the present invention, the cartilage disorder treated, prevented or ameliorated is relapsing polychondritis. Relapsing polychondritis (RP) is an uncommon and severe episodic inflammatory condition involving cartilaginous structures, predominantly those of the ear, nose, and laryngotracheobronchial tree. Other affected structures may include the eye, cardiovascular system, peripheral joints, middle ear, and inner ear.

The etiology of this disease is unknown; however, the pathogenesis is most likely autoimmune in nature. Evidence for an autoimmune etiology includes its clinical association with other autoimmune disorders, its association with the HLA-DR4 haplotype, pathology findings of infiltrating CD4 T cells and antigen-antibody complexes in the affected cartilage, cellular and humoral responses against collagen type II and other collagen antigens, and the observation that immunosuppressive regimens most often suppress the disease.

In an embodiment of the present invention, the cartilage disorder treated, prevented or ameliorated is cartilage damage resulting from a trauma. Cartilage injuries can occur as a result of traumatic mechanical destruction. A direct blow or other trauma can injure the cartilage. Cartilage has no direct blood supply, thus it has little capacity to repair itself. The methods of the present invention improve cartilage repair. Therefore in an embodiment of the present invention, cartilage damage resulting from a trauma is resulting from an accident or from surgery. In a particular embodiment of the present invention, cartilage damage resulting from a trauma is resulting from surgery, in particular orthopedic surgery or plastic surgery. Also considered by the present invention is the treatment of sport-related injury or sport-related wear of tissues of the joint.

In an embodiment of the present invention, the cartilage disorder treated, prevented or ameliorated is an unaesthetic appearance disorder. In such an embodiment, the method and use of the present invention may be used in association to plastic surgery.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE 1

Disease Models in Animals and Extended Pharmacology

In vivo, FGF-18(170AA) was tested in different disease models of OA and damaged cartilage, with significant therapeutic efficacy using an intra-articular (i.a.) dosing. Overall a therapeutically effective dose of 3-40 µg i.a. per animal/week was demonstrable in different species (rat, dog). Results from the aforementioned animal models of disease (OA as well as cartilage defects) are summarized below.

EXAMPLE 1.1

Rat Meniscal Tear Model of OA

Method

Male Lewis rats (5-10/group) underwent surgery to induce a medial meniscal tear in the right knee joint. Dosing by the i.a. route was initiated 19-21 days after surgery at doses of 0.3, 1, 3 or 10 µg (formulated in saline) to determine pharmacodynamic effects related to the dosing regimen. These total doses were administered either as (i) single dose, (ii) once weekly (⅓ of total dose per injection) for 3 weeks, or (iii) three times weekly for 3 weeks (⅑ of total dose per injection) (FIG. 1).

At the conclusion of treatment or after 3 weeks post-treatment, right knees were collected for histopathology evalua-

TABLE 1

Summary of pharmacology studies with FGF-18(170AA)

| Animal | Disease model | Dosage (µg/injection) | Route/Administration | Results |
|---|---|---|---|---|
| Rat | Injury-induced OA | 0.1, 1, 5 (formulated in hyaluronan) | Twice weekly i.a. injections for 3 weeks | Reduced cartilage degeneration<br>Reduced depth of cartilage lesions in a dose-dependent manner. Statistical significance was achieved in the 5 µg group. |
| | Meniscal tear model of OA (I) | 0.1, 1 or 10 (formulated in hyaluronan) | Twice weekly i.a. injections for 3 weeks | Reduced cartilage lesion scores in the medial tibial plateau (up to 64% decrease at 1 µg i.a.)<br>Increased tibial cartilage thickness<br>Newly generated cartilage integrated with the pre-existing cartilage<br>Increased chondrophyte size<br>Increased bone resorption/remodeling (up to 42% decreased lesion damage at 1 µg). |
| | Meniscal tear model of OA (II)[a] | 0.3, 1, 3 or 10 (formulated in saline) | i.a. injection (i) single dose, (ii) once weekly (⅓ of total dose per injection) for 3 weeks, or (iii) 3 times weekly for 3 weeks (⅑ of total dose per injection). For 3 week treatment periods, also had 3 week follow-up without treatment. | Increased periosteal stimulation<br>Improved histopathological criteria<br>Increased gross morphology repair scores<br>Dose response achieved in once weekly therapy<br>$ED_{50}$ ca 1.5 µg/joint once weekly, significant effects at 3 µg/joint once weekly |

TABLE 2

Summary of pharmacology studies with FGF-18(170AA) (continued)

| Animal | Disease model | Dosage (µg/injection) | Route/Administration | Results |
|---|---|---|---|---|
| Dog | Menisectomy OA[a] | 3, 10, 30 (formulated in saline) | i.a. injection (i) single dose, (ii) once weekly (⅓ of total dose per injection) for 3 weeks, or (iii) 3 times weekly for 3 weeks (⅑ of total dose per injection). | Improved histopathological criteria<br>Increased gross morphology repair scores<br>No clear dose-response obtained due to low number of animals involved, efficacy demonstrable at all doses applied, with more pronounced effect at 10 and 30 µg per dog i.a. |
| | Anterior cruciate ligament (ACL)[a] | 0, 3, 10, 30 | i.a. once weekly | see example 1.3. |

[a]Discussed in more detail below tion of potential effects. Evaluation of the lesions was performed in 3 different zones: regional differences across the medial tibial plateau were taken into consideration by dividing each section into 3 zones (1—outside, 2—middle, 3—inside). In the surgical OA model, the outside (z1) and middle (z2) thirds are usually most severely affected, and milder changes are present on the inside third (z3).

Experimental Design

Animals (5-10/group), housed 2-3/cage, are anesthetized with Isoflurane and the right knee area is prepared for surgery. A skin incision is made over the medial aspect of the knee and the medial collateral ligament is exposed by blunt dissection, and then transected. The medial meniscus is cut through the full thickness to simulate a complete tear. Skin and subcutis are closed with 4-0 Vicryl suture using a subcuticular pattern. Dosing by the intra-articular route is initiated 19-21 days after surgery and is discontinued after a single dose or continued for 3 weeks with intra-articular injections once per week or 3 times per week. Rats are then terminated (g1-16) or allowed to recover for an additional 3 weeks prior to termination (g17-32). Four hours prior to necropsy, all rats are given 50 mg/kg BRDU to label actively proliferating cells. Blood is collected for serum just prior to necropsy and synovial lavage is done on the right knee. At necropsy, the right (operated) knee joint was trimmed of muscle and connective tissue and collected into 10% neutral buffered formalin. The patella is removed to allow proper fixation of the joints. Trachea, sternum, and ear samples are also placed in formalin.

Results Evaluated at 6 Weeks Post Surgery

Untreated Controls (Evaluated at 6 Weeks Post Surgery)

Untreated animals with medial meniscal tear that were terminated at 6 weeks post surgery had tibial cartilage degeneration which was most severe on the outer ⅔ of the tibial plateau and less severe on the inside ⅓. Osteophytes were large (mean 468 µm). Femoral cartilage degeneration was milder and more variable than tibial degeneration. Animals treated with saline once weekly had a significantly lower zone 3 total of tibial cartilage degeneration scores (16%), a significantly lower depth ratio (16%), and a significantly greater area of viable cartilage in the lateral tibia as compared to untreated animals (13%). Animals treated with saline 3 times weekly had significantly lower cartilage degeneration scores in zone 2 of the tibia (24%), a significantly lower depth ratio (13%), and significantly greater area of viable cartilage in both the medial and lateral tibia (15 and 14%). These differences in the control groups are likely a result of repeated anesthesia events influencing overall activity of the animals, although the possibility that repeated saline injections influenced lesion severity by facilitating removal of mediators and debris cannot be ruled out.

Single Dose Treatment (Evaluated at 6 Weeks Post Surgery)

Animals given a single dose of 10 µg FGF-18(170AA) had a significantly greater width of total cartilage degeneration (16%) due to an increase in proteoglycan loss in zone 3. Osteophyte scores and measurements were significantly increased (19 and 25%, respectively) in animals given a single dose of 10 µg FGF-18(170AA). The area of viable cartilage matrix in the medial tibia was significantly increased by 27% in animals treated with 10 µg. Immunostaining revealed bromodeoxyuridine (BRDU) immunopositivity in fibrotic marrow subjacent to cartilage lesions and in bone marrow cells, fibroblasts, and osteophyte cartilage, with similar staining patterns in saline and FGF-18(170AA) treated joints. These results indicate that a single injection of 10 µg FGF-18(170AA) had a definite anabolic effect, as evidenced by increased osteophyte size and increased medial tibial cartilage area. These changes were not, however, sufficient to improve the overall cartilage degeneration scores. It is likely that the increase in medial cartilage area is a result of increased cartilage thickness on the load bearing surface adjacent to the osteophyte.

Once Weekly for 3 Weeks (Evaluated at 6 Weeks Post Surgery)

Animals treated with 3 µg FGF-18(170AA) once weekly had significantly lower cartilage degeneration scores compared to the saline once weekly control in zone 2 of the medial tibia. Animals given 10 µg FGF-18(170AA) had significantly lower significant degeneration width (37%), and those given 3 µg (28%) or 1 µg (15%) also had some inhibition. Osteophyte scores and measurements were dose responsively and significantly increased by treatment with 10 (32 and 53%) or 3 (21 and 32%) µg FGF-18(170AA). The area of viable cartilage matrix in the medial tibia was significantly increased by treatment with 10 µg FGF-18(170AA) (27%). Mild to marked chronic active synovitis with fibrosis was evident in joints injected with 10 or 3 µg and those injected with 1 µg had minimal synovitis. Subchondral bone resorption was minimally increased in a few joints treated with 10 µg. Animals treated with 3 or 10 µg FGF-18(170AA) had increased BRDU labeling in the fibrotic marrow, synovium, and in areas of chondrogenesis or osteophytes, as compared to saline controls. These results demonstrated dose responsive benefit of treatment using the once weekly paradigm on the significant cartilage degeneration width. This parameter is most indicative of the presence of a viable matrix of some type within the defect area and, along with medial tibial cartilage areas, demonstrates the anabolic response. The BRDU labeling results indicate continued proliferative responses after cessation of dosing.

Three Times Weekly for 3 Weeks (Evaluated at 6 Weeks Post Surgery)

Treatment with 1, 3 or 10 µg FGF-18(170AA) administered as 3 injections per week resulted in a significant decrease in tibial cartilage degeneration scores compared to the 3 times weekly saline control in zone 1 (animals treated with 10 µg), zone 2 (1 or 3 µg), and the zone 3 total (1 or 3 µg). Treatment with 10 µg significantly increased the total tibial cartilage degeneration width by 24%. Treatment with 1 or 3 µg nonsignificantly decreased cartilage degeneration width by 24% and 21% respectively, indicating some beneficial effect. Animals treated with 1 or 3 µg FGF-18(170AA) also had significantly lower depth ratios (17% and 18% respectively) than saline controls. The medial tibial osteophyte score was increased after treatment with 0.3, 1, 3 or 10 µg FGF-18(170AA) (13%, 7%, 13% and 15% respectively), while all 4 doses (0.3, 1, 3 or 10 µg FGF-18(170AA)) significantly increased the osteophyte measurement (12, 18, 60 and 62%, respectively. Treatment with 10 µg significantly increased the femoral cartilage degeneration score by 114%. Bone scores were significantly increased by treatment with 3 (60%) or 10 (88%) µg FGF-18(170AA). The total joint score without femur was significantly decreased by treatment with 3 µg FGF-18(170AA) (13%), but the addition of the femur to the total joint score eliminated that variation. Treatment with 1, 3 or 10 µg FGF-18(170AA) significantly increased the area of viable cartilage in the medial tibia (13%, 29% and 29%), and treatment with 3 or 10 µg significantly increased area in the lateral tibia (22% and 13%). Joints injected with 3 or 10 µg had marked to severe synovitis with increased subchondral bone resorption and similar but mild to moderate changes were observed in joints treated with 1 µg. Animals treated with 1, 30 or 10 µg FGF-18(170AA) had BRDU labeling in numerous areas including marrow, osteophytes, meniscus, synovium, and areas of chondrogenesis. These results demonstrated the most pronounced anabolic effects of any treatment paradigm, but were accompanied by severe synovial inflammation and increased subchondral bone resorption.

Results Evaluated at 9 Weeks Post Surgery

Untreated Controls (Evaluated at 9 Weeks Post Surgery)

Untreated animals with medial meniscal tear that were terminated at 9 weeks had tibial cartilage degeneration which was most severe on the outer ⅔ of the tibial plateau and less severe on the inside ⅓. Femoral cartilage degeneration was less severe and more variable. Scores were, in general, higher than in untreated animals terminated at week 6. Single dose saline controls had significantly lower cartilage degeneration scores in zone 2 of the tibia (12%) than those of the once weekly saline controls (18%). Single dose saline controls also had significantly greater width of moderate collagen degeneration (92%). Animals given saline once weekly had a significantly lower sum of severe, marked, moderate, and mild collagen degeneration (15%), as those of the 3 times weekly saline control animals (22%). These differences were relatively minor since there were only 5 rats in each of these groups and were a result of variation in disease progression in individuals.

Single Dose (Evaluated at 9 Weeks Post Surgery, Incl. 3 Weeks Post-Treatment)

There was no significant effect of treatment in any animals given a single dose of FGF-18(170AA) and terminated 9 weeks after surgery, although a few joints injected with 10 μg had evidence of anabolic response on the lateral tibia.

Once Weekly for 3 Weeks (Evaluated at 9 Weeks Post Surgery, Incl. 3 Weeks Post-Treatment)

After treatment with 10 μg FGF-18(170AA) once weekly, significant decreases in cartilage degeneration scores in zone 1 and zone 3 total of the medial tibia by 38 and 31% were observed. Treatment with 0.3 μg FGF-18(170AA) significantly reduced scores in zone 2 compared to the once weekly saline control. Animals treated with 10 μg FGF-18(170AA) had significantly lower significant cartilage degeneration width (38%). Depth ratios were significantly decreased by treatment with 10 μg FGF-18(170AA) (22%). Treatment with 3 or 10 μg FGF-18(170AA) significantly and identically increased osteophyte scores (25%), but only animals given 10 μg had significantly increased osteophyte measurements (53%). There was a 23% significant decrease in total joint score with femur in animals given 10 μg FGF-18(170AA). The area of viable cartilage was significantly increased in animals given 10 μg FGF-18(170AA) in both the medial (40%) and lateral (81%) tibia. Treatment with 10 μg FGF-18 (170AA) significantly reduced the width of severe and minimal collagen degeneration, as well as the width of severe, marked, and moderated degeneration combined and the width of severe and marked combined. Synovial inflammation was minimal in joints injected with 3 or 10 μg and absent at lower doses. Anabolic responses were evident in some or all joints injected with any dose. BRDU labeling was seen mainly in bone marrow and fibroblasts of saline controls and increased labeling (cartilage and osteophytes) was seen in joints injected with 10 μg. These results indicated that the cartilage repair/anabolic responses continued beyond the treatment period and that synovitis subsided, although osteophyte measures were comparable at 6 or 9 weeks in joints treated with this dose. Dose responsive benefit was seen using the significant cartilage degeneration parameter and severe matrix loss, as measured by collagen degeneration, was improved.

Three Times Weekly for 3 Weeks (Evaluated at 9 Weeks Post Surgery, Incl. 3 Weeks Post-Treatment)

The zone 3 total tibial cartilage degeneration score was significantly decreased by 38% in animals given 10 μg FGF-18(170AA) as 3 injections weekly, as compared to the 3 times weekly saline control. Treatment with 10 μg FGF-18(170AA) also significantly decreased the significant cartilage degeneration width (48%). The depth ratio was significantly decreased by 27% in animals treated with 10 μg FGF-18 (170AA). Osteophyte measurements were significantly increased in animals treated with 3 (57%) or 10 (103%) μg FGF-18(170AA). Treatment with 1, 3, or 10 μg FGF-18 (170AA) significantly increased the area of viable cartilage in the medial tibia (34%, 37% and 71% respectively), while treatment with 0.3 or 10 μg FGF-18(170AA) significantly increased areas in the lateral tibia (46% and 67%). Mild collagen degeneration width was significantly increased in animals treated with 3 or 10 μg FGF-18(170AA), as was the width of mild and minimal degeneration combined in animals given 10 μg. Mild synovitis was present in all joints injected with 10 μg (divided) and minimal to mild synovitis was present in those given 1 or 3 μg. Anabolic responses were evident from 1 μg upwards. BRDU labeling was seen mainly in bone marrow and fibroblasts of saline controls and increased labeling (cartilage and osteophytes) was seen in joints injected with 10 μg. These results indicated that the cartilage repair/anabolic responses continued beyond the treatment period and that synovitis subsided as compared to the 6 week time point. Beneficial effects on collagen loss were less clear, although there was a definite trend towards smaller measurements for the areas of marked to severe loss.

EXAMPLE 1.2

Dog Menisectomy Model of OA

Female beagle dogs (n=3/group) that had had unilateral partial medial menisectomy on the left knee one month prior to initiation of treatment were treated with saline or 3, 10, or 30 μg FGF-18(170AA) once, once weekly, or three times weekly (divided ⅓ doses) for 3 weeks to determine beneficial effects on established OA.

After 3 weeks of treatment, left knees were evaluated for effects on gross (n=3/group) and microscopic (n=3/group) changes induced by menisectomy and for evidence of anabolic effects. All dogs except one exhibited normal appetite and activity throughout the study. One dog (YLI-8) from group 12 died prior to termination (day 17) due to aspiration pneumonia associated with repeated anesthesia for joint injections. Typical degenerative changes characterized by the presence of focal, well circumscribed lesions of cartilage degeneration were present on the medial tibias of all operated dogs in all groups. Femoral lesions were sporadically observed. All dogs had minimal medial joint capsule thickening. Meniscal damage (approximately ½ absent at necropsy with generally none to moderate repair) was similar in all groups.

Microscopic evaluation revealed that untreated and vehicle treated knees often had cartilage hypertrophy with cloning in the zone 1 of levels 1 and 2. Definite anabolic effects (increased cloning, cellularity, and proteoglycan staining in lesion areas) were observed in knees treated with 30 μg (10 μg three times weekly) FGF-18(170AA), and these changes were most identifiable on femoral condyles. Lesser, but still convincing anabolic effects were observed in some knees treated 3 times weekly with the lower doses of FGF-18 (170AA), or in knees treated with 30 or 10 μg once weekly.

When present, these FGF-18(170AA) induced changes were generally in the upper ⅓ to ½ of the cartilage or in matrix adjacent to deeper clefts.

Results of this study demonstrated definite anabolic effects of i.a. treatment with 10 μg FGF-18(170AA) 3 times weekly (30 μg total/week) in all knees and lesser effects in some knees treated with lower doses 3 times weekly or with 30 or 10 μg once weekly. The changes consisted of cloning, increased proteoglycan synthesis in the upper ⅓ to ½ of the cartilage or in matrix adjacent to clefts. Mild marginal zone proliferative changes were observed in some joints but there were no excessive changes similar to those occurring in rats. The anabolic changes in articular cartilage were greater than the anabolic changes in marginal zones in all cases. Collagen damage measurements also suggested some protection of matrix integrity.

EXAMPLE 1.3

Dog Anterior Cruciate Ligament (ACL) Model

For investigations on severe progressive osteoarthritis, the dog anterior cruciate ligament (ACL) model is used for preclinical pharmacology investigations, including MRI evaluation at end of treatment and at follow up. This model provides efficacy data (histopathological and MRI over time and follow up) together with data on function by means of gait analysis.

Using a non-invasive read-out MRI already at end of treatment a decrease in cartilage lesions compared to healthy baseline was demonstrable (−13.3, −7.5, −9.3 and −8.8 for vehicle, 3 μg/joint, 10 μg/joint and 30 μg/joint, respectively). Also a functional improvement measured via gait analysis on force plate is demonstrable at end of therapy:

Gait analysis was performed using a platform-based pressure/force measurement (Matscan® System, Tekscan Inc, Boston, Mass., USA).

Gait Acquisition Procedures

The Matscan® System comprises 4 walkway floor displays, each having 2,288 sensing elements included in a sensing area of 432 mm×368 mm, producing a spatial resolution of 1.4 sensels/cm2. This device was calibrated with a predefined weight at the beginning of the study and the same calibration was used for all dogs throughout the study.

For the osteoarthritis-induced hind limb, the peak vertical force and the contact area were acquired at a trotting gait velocity ranging from 1.9 to 2.2 meters/second. Velocity was ensured using a chronometer. The gait acquisition window was 3 seconds with a sampling rate set at 44 hertz, producing a total of 132 frames. The first 5 valid trials were obtained for each dog and then averaged to characterize the dog profile at a given point in time. The peak vertical force was expressed in percentage of body weight (% BW) and the contact area was expressed in square centimeters (cm2).

With regard to the peak vertical force of the osteoarthritis-induced hind limb acquired at the trot, the canine osteoarthritis model produced an abnormal gait (week 4) discernable over pre-operative values (baseline). The peak vertical force and the contact area were decreased 4 and 8 weeks following surgery as negative changes were observed in all groups (Tables 3 & 4). There was however a trend for dogs in Group IV at 8 weeks following surgery to have a less severe decrease compared to baseline vis-à-vis the other groups.

TABLE 3

Peak Vertical Force Acquired At The Trot (Dynamic Event) For The Osteoarthritis-Induced Hind Limb

| Group | Animals (n) | Peak vertical force[a] | |
|---|---|---|---|
| | | Week 4 (% BW)[b] | Week 8 (% BW)[b] |
| I OA: placebo control | 8 | −37.34 ± 5.68 | −27.45 ± 3.90 |
| II FGF-18: 3 μg/joint | 8 | −34.84 ± 3.65 | −22.08 ± 2.87 |
| III FGF-18: 10 μg/joint | 8 | −36.59 ± 3.14 | −25.11 ± 3.03 |
| IV FGF-18: 30 μg/joint | 8 | −32.28 ± 3.05 | −15.71 ± 1.85 |

[a]Values presented are Mean ± SEM. Values are the changes over baseline.
[b]Values are expressed in percentage of body weight (% BW).

TABLE 4

Contact Area Acquired At The Trot (Dynamic Event) For The Osteoarthritis-Induced Hind Limb

| Group | Animals (n) | Contact area[a] | |
|---|---|---|---|
| | | Week 4 (cm$^2$)[b] | Week 8 (cm$^2$)[b] |
| I OA: placebo control | 8 | −11.17 ± 2.61 | −7.11 ± 1.55 |
| II FGF-18: 3 μg/joint | 8 | −11.50 ± 1.41 | −4.95 ± 0.78 |
| III FGF-18: 10 μg/joint | 8 | −10.45 ± 1.63 | −4.92 ± 1.47 |
| IV FGF-18: 30 μg/joint | 8 | −10.22 ± 1.52 | −3.90 ± 0.93 |

[a]Values presented are Mean ± SEM. Values are the changes over baseline.
[b]Values are expressed in square centimeters (cm$^2$).

The results of in vitro pharmacology demonstrated specific activity on chondrocytes (proliferation and cartilage regeneration/collagen synthesis) and the absence of adverse effects like leukocyte proliferation or cytokine release by different cell types after exposure to FGF-18(170AA).

EXAMPLE 1.4

Investigations Using Radiolabelled FGF18 [3H]-FGF18

The levels of radioactivity found in the joint knee articulation following intra-articular administration of [3H]-FGF18 are reported in table 5 (as concentrations of total radioactivity, expressed as ng equivalents/g) and in table 6 (expressed as percentages of administered dose); in the tables are reported the radioactivity levels determined in the treated articulations analyzed both as intact knee joint and after collection of the synovial fluid. The corresponding pharmacokinetic parameters in joint knee articulation, either with or without the synovial fluid, are reported in table 7.

TABLE 5

Concentrations of total radioactivity in joint knee articulation following a single intra-articular administration of [³H]-AS902330 at a target dose level of 0.24 mg/kg to male rats.

| Sample | Time | Group 4 whole articulation | Group 3 without synovial fluid | Ratio Without synovial fluid/whole articulation |
|---|---|---|---|---|
| KNEE JOINT | 15 m | 26037 | 11740 | 0.45 |
|  | 1 h | 13320 | 9086.7 | 0.68 |
|  | 4 h | 15270 | 9664.1 | 0.63 |
|  | 24 h | 6167.9 | 4054.3 | 0.66 |
|  | 48 h | 3376.3 | 1450.8 | 0.43 |

Results are expressed as ng equivalents/g.

TABLE 6

Recovery of total radioactivity from joint knee articulation following a single intra-articular administration of [³H]-AS902330 at a target dose level of 0.24 mg/kg to male rats.

| Sample | Time | Group 4 whole articulation | Group 3 without synovial fluid | Ratio Without synovial fluid/whole articulation |
|---|---|---|---|---|
| KNEE JOINT | 15 m | 87.87 | 66.23 | 0.75 |
|  | 1 h | 78.43 | 67.39 | 0.86 |
|  | 4 h | 70.94 | 40.92 | 0.58 |
|  | 24 h | 28.62 | 14.09 | 0.49 |
|  | 48 h | 21.61 | 8.29 | 0.38 |

Results are expressed as % of administered dose.

TABLE 7

Systemic exposure parameters of total radioactivity in joint knee articulation following a single intra-articular administration of [³H]-AS902330 at a target dose level of 0.24 mg/kg to male rats.

|  | Group 3 Without synovial fluid | Group 4 Whole articulation | Ratio Without synovial fluid/whole articulation |
|---|---|---|---|
| $C_{max}$ (ngeq/g) | 11740 | 26037 | 0.45 |
| Regression range | 4-48 | 4-48 |  |
| $t^{1/2}$, z (hr) | 16 | 20 |  |
| AUC(0-tlast) (ngeq · h/gr) | 242116 | 393063 | 0.62 |
| AUC(0-∞) (ngeq · h/gr) | 275787 | 492380 | 0.56 |

The levels of total radioactivity in the treated articulation declined bi-phasically (, with a terminal half-life of 20 hours. A comparable value was obtained taking into account the whole articulation without synovial fluid (16 hours). Overall, the results indicated that the total radioactivity distributed outside the synovial fluid into the tissues of the knee articulation. The results obtained after autoradioluminography analysis of the treated knee joints shown that most of the radioactivity was localized in close proximity to the articulation.

The results of whole body autoradioluminography analyses after intravenous administration and intra-articular administration of [³H]-FGF18 are reported in table 8 and in table 9, respectively. Concentrations of total radioactivity in tissues and organs are expressed as ng equivalents/g (Mean±SD).

TABLE 8

Concentrations of total radioactivity following a single intravenous administration of [³H]-AS902330 at a target dose level of 0.24 mg/kg to male rats (Group 1). Results are expressed as ng equivalents/g (Mean ± SD).

| TISSUE | 0.25 h Mea | 0.25 h S.D. | 1 h Mea | 1 h S.D. | 4 h Mea | 4 h S.D. | 24 h Mea | 24 h S.D. | 48 h Mea | 48 h S.D. |
|---|---|---|---|---|---|---|---|---|---|---|
| Adrenal Glands |  |  |  |  | 3890 | 2410 | 480 | 20 | 180 |  |
| Blood |  |  |  |  | 110 | 50 |  |  |  |  |
| Bone marrow |  |  |  |  | 460 | 120 | 790 | 210 | 420 | 90 |
| Kidney |  |  |  |  | 1170 | 400 | 770 | 180 | 440 | 220 |
| Liver |  |  |  |  | 1210 | 260 | 560 | 110 | 310 | 150 |
| Lung |  |  |  |  | 200 | 90 | 150 | 40 |  |  |
| Pancreas |  |  |  |  | 210 | 40 | 220 | 60 | 80 | 20 |
| Salivary glands |  |  |  |  | 220 | 111 | 270 | 50 | 111 | 30 |
| Spleen |  |  |  |  | 690 | 260 | 440 | 30 | 260 | 40 |
| Testis |  |  |  |  |  |  | 90 | 20 |  |  |
| Thymus |  |  |  |  |  |  | 280 | 50 | 170 |  |

* NQ: Not quantifiable (below limit of quantification)

TABLE 9

Concentrations of total radioactivity following a single intra-articular administration of [³H]-AS902330 at a target dose level of 0.24 mg/kg to male rats (Group 2). Results are expressed as ng equivalents/g (Mean ± SD).

| TISSUE | 0.25 h | | 1 h | | 4 h | | 24 h | | 48 h | |
|---|---|---|---|---|---|---|---|---|---|---|
| | Me | S.D | Mean | S.D | Mean | S.D. | Mean | S.D. | Mean | S.D. |
| Adrenal | | | | | | | | | | |
| Bone marrow | | | | | | | 170 | | 190 | 20 |
| Kidney | | | | | 120 | 20 | 90 | 20 | 90 | 30 |
| Liver | | | | | 60 | 0.0 | 70 | 10 | 70 | 20 |
| Pancreas | | | | | | | | | | |
| Salivary | | | | | | | | | | |
| Spleen | | | | | | | | | 90 | 20 |
| Thymus | | | | | | | | | | |
| Knee Joint | | | | | 10720 | 57940 | 4128 | 2448 | 1184 | 4230 |

* NQ: Not quantifiable (below limit of quantification)

After intravenous administration the total radioactivity in blood and serum reached the highest value at 4 hours and 24 hours after administration, in serum and blood, respectively. The measured half live in serum was about 55 hours. After intra-articular administration the means of total radioactivity increased slowly reaching the highest concentration at 24 and 48 hours after administration, in serum and blood, respectively. The systemic exposure was approximately 20% of that found after intravenous administration.

Total radioactivity in serum was on average higher than that in blood, suggesting that the parent compound and/or its metabolites had low affinity for blood cells and circulating radioactivity was mainly distributed in serum.

The levels of total radioactivity in the treated articulation declined bi-phasically with a terminal half-life of 20 hours.

Overall, the results indicated that the total radioactivity distributed outside the synovial fluid into the knee articulation.

Overall, based on the non-clinical pharmacology models in rat and dog, it is found that a particularly appropriate dosing regimen is once weekly for three weeks. The effective dose observed varies from 3-30 µg/joint.

EXAMPLE 2

Examples of FGF-18 Compounds of the Invention

Sequences of preferred FGF-18 compounds of the invention are given in the sequence listing hereinbelow.

The invention claimed is:

1. A method for treating a patient having a cartilage disorder characterized by cartilage injury or a loss of cartilage in a joint comprising the intraarticular administration of an FGF-18 compound to a mammalian patient having a cartilage disorder, wherein the FGF-18 compound is administered in a treatment cycle that comprises the administration of said FGF-18 compound at least three times and each administration is separated by at least 6 days, wherein said FGF-18 compound is intraarticularly administered into a joint in which cartilage has been lost or injured and said treatment results in an increase in cartilage deposition in said joint of said mammalian patient, and wherein said FGF-18 compound comprises amino acid residues 28 to 207 of SEQ ID NO: 2 or SEQ ID NO: 5 (FGF-18 (170AA)).

2. The method according to claim 1, wherein each administration is separated by 7 days.

3. The method according to claim 1, wherein said treatment cycle comprises the administration of said FGF-18 compound once per week for at least 3 consecutive weeks.

4. The method according to claim 1, wherein said treatment cycle comprises the administration of said FGF-18 compound once per week for 3 consecutive weeks.

5. The method according to claim 1, wherein treatment cycles are repeated 2, 4, 6 or 8 months after the first administration of said FGF-18 compound.

6. The method according to claim 1, said method comprising 1, 2, 3, 4, 5 or 6 treatment cycles per year.

7. The method according to claim 1, said method comprising the administration of said FGF-18 compound at a dose of: 3-100 mcg; 5-40 mcg; or 10-30 mcg per single intra-articular administration.

8. The method according to claim 7, said method comprising the administration of said FGF-18 compound at a dose of 3-100 mcg per single intra-articular administration.

9. The method according to claim 7, said method comprising the administration of said FGF-18 compound at a dose of 5-40 mcg per single intra-articular administration.

10. The method according to claim 7, said method comprising the administration of said FGF-18 compound at a dose of 10-30 mcg per single intra-articular administration.

11. The method according to claim 1, said method comprising the administration of said FGF-18 compound at a dose of about 3, 5, 10, 15, 20, 25, 30, 35, 40, 45, 50, 55, or 60 mcg per single intra-articular administration.

12. The method according to claim 1, wherein the FGF-18 compound comprises SEQ ID NO: 5 (FGF-18(170AA)).

13. The method according to claim 1, wherein said administrations are separated by 6 days.

14. The method according to claim 1, wherein said administrations are separated by 8 days.

15. The method according to claim 1, wherein said treatment cycle comprises the administration of said FGF-18 compound once per week for 4 consecutive weeks.

16. A method of treating a patient having cartilage injury comprising administering a FGF-18 compound to a mammalian patient having a cartilage injury, wherein said FGF-18 compound is administered intraarticularly in a treatment cycle that comprises the administration of said FGF-18 compound at least three times and each administration is separated by at least 6 days and said treatment increases cartilage deposition in a joint of said mammalian patient, and wherein said FGF-18 compound comprises amino acid residues 28 to 207 of SEQ ID NO: 2 or SEQ ID NO: 5 (FGF-18 (170AA)).

17. The method according to claim 16, wherein said FGF-18 compound is administered in a treatment cycle that comprises the administration of said FGF-18 compound once per week for 3 consecutive weeks.

18. The method according to claim 17, wherein said FGF-18 compound comprises amino acid residues 28-207 of SEQ ID NO: 2.

19. The method according to claim 17, wherein said FGF-18 compound comprises SEQ ID NO: 5 (FGF-18(170AA)).

20. The method according to claim 16, wherein said FGF-18 compound is administered in a treatment cycle that comprises the administration of said FGF-18 compound once per week for 4 consecutive weeks.

21. The method according to claim 16, wherein said FGF-18 compound comprises amino acid residues 28-207 of SEQ ID NO: 2.

22. The method according to claim 16, wherein said FGF-18 compound comprises SEQ ID NO: 5 (FGF-18(170AA)).

23. The method according to claim 16, wherein treatment cycles are repeated 2, 4, 6, or 8 months after the first administration of said FGF-18 compound.

24. The method according to claim 16, said method comprising 1, 2, 3, 4, 5, or 6 treatment cycles per year.

25. A method for treating a patient having osteoarthritis comprising the intraarticular administration of an FGF-18 compound comprising amino acid residues 28 to 207 of SEQ ID NO: 2 or SEQ ID NO: 5 (FGF-18 (170AA)) into an osteoarthritic joint of a mammalian patient, wherein the FGF-18 compound is administered in a treatment cycle that comprises the administration of said FGF-18 compound at least three times, each administration is separated by at least 6 days and treatment results in an increase in cartilage deposition in said osteoarthritic joint.

26. The method according to claim 25, wherein the osteoarthritis is knee osteoarthritis or hip osteoarthritis or secondary hip osteoarthritis.

27. The method according to claim 25, wherein said FGF-18 compound is administered in a treatment cycle that comprises the administration of said FGF-18 compound once per week for 3 consecutive weeks.

28. The method according to claim 25, wherein said FGF-18 compound is administered in a treatment cycle that comprises the administration of said FGF-18 compound once per week for 4 consecutive weeks.

29. The method according to claim 28, wherein said FGF-18 compound comprises amino acid residues 28-207 of SEQ ID NO: 2.

30. The method according to claim 28, wherein said FGF-18 compound comprises SEQ ID NO: 5 (FGF-18(170AA)).

31. The method according to claim 25, wherein said FGF-18 compound comprises amino acid residues 28-207 of SEQ ID NO: 2.

32. The method according to claim 25, wherein said FGF-18 compound comprises SEQ ID NO: 5 (FGF-18(170AA)).

33. The method according to claim 25, wherein treatment cycles are repeated 2, 4, 6 or 8 months after the first administration of said FGF-18 compound.

34. The method according to claim 25, said method comprising 1, 2, 3, 4, 5 or 6 treatment cycles per year.

* * * * *

UNITED STATES PATENT AND TRADEMARK OFFICE
CERTIFICATE OF CORRECTION

PATENT NO. : 8,207,115 B2
APPLICATION NO. : 12/374488
DATED : June 26, 2012
INVENTOR(S) : Alberto Gimona et al.

Page 1 of 1

It is certified that error appears in the above-identified patent and that said Letters Patent is hereby corrected as shown below:

Column 2,
Line 23, "method permits" should read --method permit--.

Column 5,
Line 13, "modified from" should read --modified form--.
Line 42, "natural occurring" should --naturally occurring--.

Column 6,
Line 23, "as component" should read --as a component--.

Column 7,
Line 60, "for 30 60 minutes" should read --for 30-60 minutes--.

Column 13,
Lines 14-15, "occurs naturally occurring within" should read --occurs naturally within--.
Line 28, "more commonly than" should read --more commonly affected than--.

Column 22,
Lines 50-51, "and 62%, respectively." should read --and 62%, respectively).--.

Column 28,
Line 25, "shown" should read --showed--.

Signed and Sealed this
Twelfth Day of February, 2013

Teresa Stanek Rea
*Acting Director of the United States Patent and Trademark Office*